(12) United States Patent
Beck et al.

(10) Patent No.: US 9,861,744 B2
(45) Date of Patent: Jan. 9, 2018

(54) MANAGING BLOOD GLUCOSE LEVELS

(75) Inventors: Randall Beck, Cary, NC (US); Jeffrey M. Eichen, Apex, NC (US); Dale R. Hille, Raleigh, NC (US); Jan Rogoyski, Pflugerville, TX (US); Jerry A. Williams, Montezuma, IA (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 256 days.

(21) Appl. No.: 13/532,328

(22) Filed: Jun. 25, 2012

(65) Prior Publication Data

US 2013/0345664 A1    Dec. 26, 2013

(51) Int. Cl.
*A61M 31/00*  (2006.01)
*A61M 5/172*  (2006.01)

(52) U.S. Cl.
CPC .................. *A61M 5/1723* (2013.01)

(58) Field of Classification Search
CPC ...... A61M 5/1723; A61M 5/168; G04B 37/12
USPC ....... 604/504, 65, 890.1, 6, 66, 503; 368/10, 368/12, 278
See application file for complete search history.

(56) References Cited

U.S. PATENT DOCUMENTS

| | | | | |
|---|---|---|---|---|
| 6,464,389 | B1 * | 10/2002 | Ghoorahoo | A61J 7/0481 368/223 |
| 7,598,878 | B2 * | 10/2009 | Goldreich | 340/573.1 |
| 2003/0036683 | A1 * | 2/2003 | Kehr | G06F 19/325 600/300 |
| 2003/0208110 | A1 | 11/2003 | Mault | |
| 2005/0116820 | A1 * | 6/2005 | Goldreich | A61B 5/0002 340/539.12 |
| 2006/0276702 | A1 | 12/2006 | McGinnis | |
| 2007/0131573 | A1 | 6/2007 | Boyles | |
| 2008/0085331 | A1 * | 4/2008 | Gluskin | A61K 31/70 424/758 |
| 2009/0054735 | A1 | 2/2009 | Higgins et al. | |
| 2009/0069787 | A1 * | 3/2009 | Estes | A61M 5/1413 604/503 |
| 2009/0299276 | A1 * | 12/2009 | Brauker | A61B 5/0002 604/66 |

(Continued)

FOREIGN PATENT DOCUMENTS

WO        9838909 A1    9/1998

OTHER PUBLICATIONS

"Continuous Glucose Monitoring", Medtronic, published on the world wide web at http://www.medtronicdiabetes.com/products/continuousglucosemonitoring.

(Continued)

*Primary Examiner* — Kevin C Sirmons
*Assistant Examiner* — Tiffany Legette-Thompson
(74) *Attorney, Agent, or Firm* — Paul S. Drake

(57) ABSTRACT

A method, computer usable program product, or a system for managing a blood glucose level of a person including providing a device worn exterior to the person for monitoring a set of treatment factors and a set of environmental factors associated with the person, predicting a blood glucose level for the person based on the set of treatment factors and the set of environmental factors, and responsive to predicting a blood glucose level for the person dropping lower than a predetermined minimum value, supplying carbohydrates to the person.

20 Claims, 9 Drawing Sheets

(56) References Cited

U.S. PATENT DOCUMENTS

| | | | |
|---|---|---|---|
| 2010/0057043 A1* | 3/2010 | Kovatchev | A61B 5/024 604/504 |
| 2010/0211005 A1* | 8/2010 | Edwards | A61M 5/002 604/82 |
| 2010/0292634 A1* | 11/2010 | Kircher, Jr. | A61B 5/14532 604/66 |
| 2010/0319436 A1* | 12/2010 | Sun | A61B 5/01 73/61.46 |
| 2011/0028803 A1* | 2/2011 | Ollmar | 600/301 |
| 2011/0050428 A1* | 3/2011 | Istoc | G06F 19/345 340/573.1 |
| 2011/0174638 A1* | 7/2011 | Katsuki | A61B 5/14503 205/792 |
| 2011/0191059 A1* | 8/2011 | Farrell | A61B 5/14532 702/130 |
| 2012/0095303 A1* | 4/2012 | He | 600/301 |

OTHER PUBLICATIONS

Suunto Fitness and Endurance Products, Suunto, published on the world wide web at http://www.suunto.com/en-US/.
Wristbands, Lance Armstrong Foundation, published on the world wide web at http://www.store-laf.org/wristbands.html.

* cited by examiner

MANAGING BLOOD GLUCOSE LEVELS

BACKGROUND

1. Technical Field

The present invention relates generally to managing blood glucose levels, and in particular, to a computer implemented method for predicting and responding to a low blood glucose condition.

2. Description of Related Art

Diabetes is a chronic condition in which a person has high blood glucose (sugar), either because the body does not produce enough insulin, or because cells do not respond to the insulin that is produced. Insulin is a hormone that reduces blood glucose. Insulin is produced by the pancreas in response to increased blood glucose levels. Insulin causes cells in the liver, muscle and fat tissue to take up glucose from the blood, storing it as glycogen inside these tissues.

There are several types and causes of diabetes. Type 1 diabetes results from the body's failure to produce insulin. Type 2 diabetes results from insulin resistance, a condition in which cells fail to use insulin properly to reduce blood glucose properly, sometimes combined with an insulin deficiency. Gestational diabetes may occur in pregnant women, which may precede Type 2 diabetes. There are congenital diabetes due to genetic defects of insulin secretion, cystic fibrosis-related diabetes, steroid diabetes induced by high doses of glucocorticoids, and several other forms of diabetes.

Type 1 diabetes presently requires the person to inject insulin either with a syringe or an insulin pump to manage blood glucose levels. The other types of diabetes may also require the use of injected insulin depending on the severity of the condition and the ability of the person to manage their diabetes such as through diet and exercise. A normal range of blood glucose (sugar) is between 70 and 100 milligrams per deciliter (mg/dl) in the morning up to 135 to 140 mg/dl after a meal. When a person experiences elevated blood sugars over a period of time, various medical conditions can occur including damage to the heart, kidneys, nerves, eyes, and elsewhere throughout the body. As a result, a person with poorly managed diabetes may suffer from heart disease, kidney disease, blindness, circulation issues leading to amputations, etc.

Before the advent of the modern insulin pump, a diabetic would inject insulin using syringes, typically before and/or after a meal. The person would estimate the amount a calories being consumed and then calculate the appropriate amount of insulin to be injected. However, a person with diabetes could easily underestimate or overestimate the number of calories being consumed, and/or not take into account other influential factors, such as exercise or time since the last meal, thereby resulting in excessive swings in blood glucose levels.

Today many diabetics, particularly Type 1 diabetics, may use an insulin pump to deliver insulin. This pump can provide a steady infusion of insulin known as a basal rate between meals. The insulin pump can also provide an increased dose of insulin known as a bolus during meal periods based on the estimated amount of carbohydrates ingested, as entered by the diabetic into the insulin pump. The insulin pump recommends and implements an insulin dose based on the intended amount of food intake using a "Bolus Wizard" (a software program term known to many users of insulin pumps). The bolus wizard uses information provided by the patient's health care professional. For example, a ratio of 12:1 may apply for a given patient meaning the consumption of 24 grams of carbohydrates requires an injection of 2 grams of insulin.

Hypoglycemia or low blood glucose is an abnormally low amount of glucose in the blood. For a normal person, hypoglycemia may occur when their blood glucose drops below 70 mg/dl. For diabetics, hypoglycemia may occur at higher blood glucose levels such as 80 or even 90 mg/dl. Hypoglycemia may cause several initial symptoms such as double vision, increased heart rate, nervousness and confusion, shaking or trembling, sweating, etc. However, a diabetic may not show these initial symptoms of hypoglycemia, a condition referred to as hypoglycemia unawareness. Hypoglycemia may be caused by 1) too much insulin being released in the bloodstream such as by injection, 2) the body's glucose is used up too quickly such as by exercise, or 3) glucose is released into the bloodstream too slowly such as by inadequate consumption of carbohydrates. Hypoglycemia can be a dangerous condition, yet can be easily treated initially by consuming some carbohydrates such as by drinking a sweet soft drink. If not treated, hypoglycemia could result in confusion, fainting, seizures, coma and even death.

SUMMARY

The illustrative embodiments provide a method, computer usable program product, and a system for managing a blood glucose level of a person including providing a device worn exterior to the person for monitoring a set of treatment factors and a set of environmental factors associated with the person, predicting a blood glucose level for the person based on the set of treatment factors and the set of environmental factors, and responsive to predicting a blood glucose level for the person dropping lower than a predetermined minimum value, supplying carbohydrates to the person.

BRIEF DESCRIPTION OF THE SEVERAL VIEWS OF THE DRAWINGS

The novel features believed characteristic of the invention are set forth in the appended claims. The invention itself, further objectives and advantages thereof, as well as a preferred mode of use, will best be understood by reference to the following detailed description of illustrative embodiments when read in conjunction with the accompanying drawings, wherein:

DETAILED DESCRIPTION

Steps may be taken to manage blood glucose levels. These steps may be taken as will be explained with reference to the various embodiments below.

Figure 1:
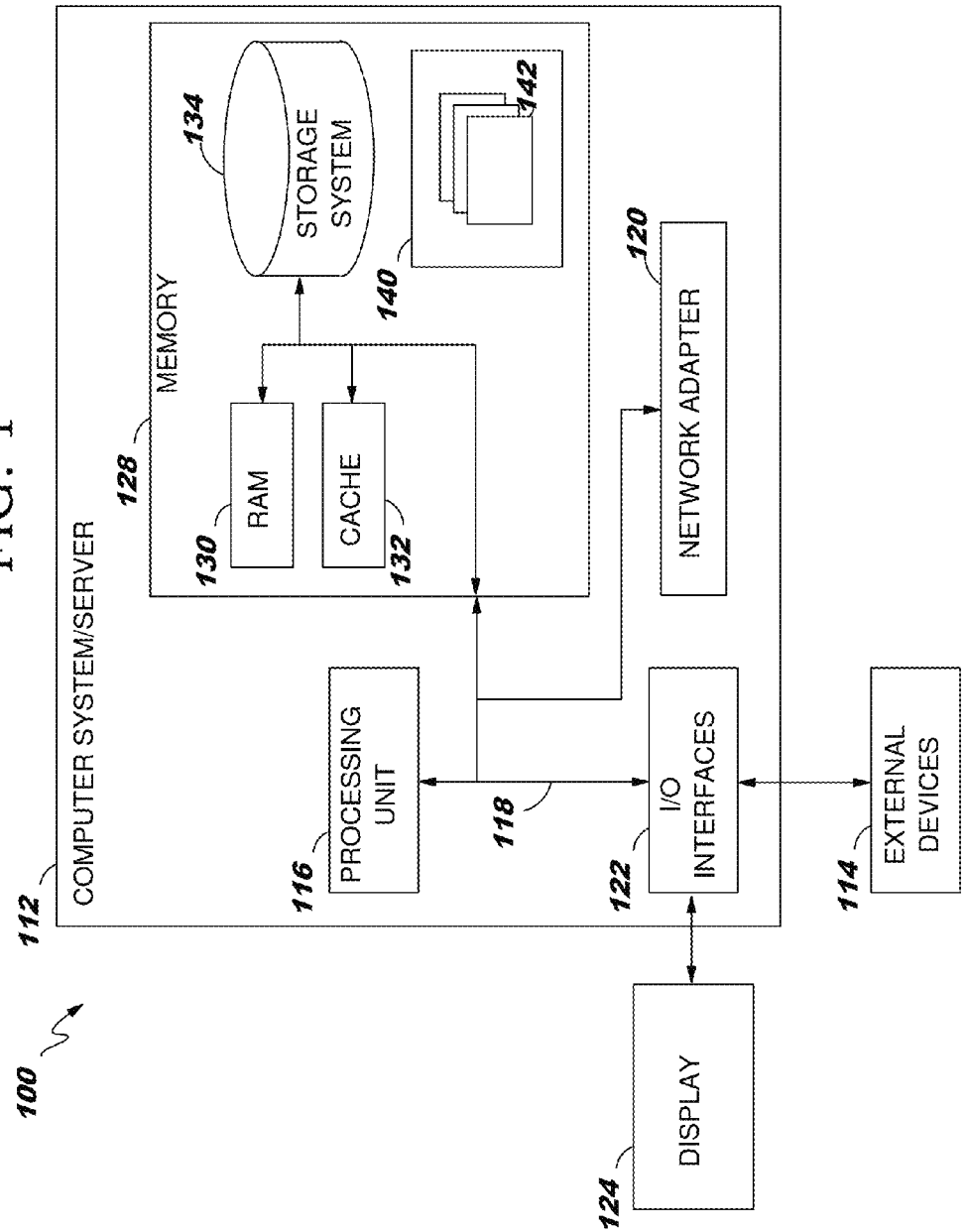
FIG. 1 is a block diagram of a data processing system in which various embodiments may be implemented.

FIG. 1 is a block diagram of a data processing system in which various embodiments may be implemented. Data processing system 100 is only one example of a suitable data processing system and is not intended to suggest any limitation as to the scope of use or functionality of embodiments of the invention described herein. Regardless, data processing system 100 is capable of being implemented and/or performing any of the functionality set forth herein.

In data processing system 100 there is a computer system/server 112, which is operational with numerous other general purpose or special purpose computing system environments, peripherals, or configurations. Examples of well-known computing systems, environments, and/or configurations that may be suitable for use with computer system/server 112 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 112 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 112 may be practiced in distributed computing environments where tasks are performed by remote processing devices that are linked through a communications network. In a distributed computing environment, program modules may be located in both local and remote computer system storage media including memory storage devices.

As shown in FIG. 1, computer system/server 112 in data processing system 100 is shown in the form of a general-purpose computing device. The components of computer system/server 112 may include, but are not limited to, one or more processors or processing units 116, a system memory 128, and a bus 118 that couples various system components including system memory 128 to processor 116.

Bus 118 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 112 typically includes a variety of computer system readable media. Such media may be any available media that is accessible by computer system/server 112, and it includes both volatile and non-volatile media, removable and non-removable media.

System memory 128 can include computer system readable media in the form of volatile memory, such as random access memory (RAM) 130 and/or cache memory 132. Computer system/server 112 may further include other removable/non-removable, volatile/non-volatile computer system storage media. By way of example only, storage system 134 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 118 by one or more data media interfaces. Memory 128 may include at least one program product having a set (e.g., at least one) of program modules that are configured to carry out the functions of embodiments of the invention. Memory 128 may also include data that will be processed by a program product.

Program/utility 140, having a set (at least one) of program modules 142, may be stored in memory 128 by way of example, and not limitation, as well as an operating system, one or more application programs, other program modules, and program data. Each of the operating system, one or more application programs, other program modules, and program data or some combination thereof, may include an implementation of a networking environment. Program modules 142 generally carry out the functions and/or methodologies of embodiments of the invention. For example, a program module may be software for managing blood glucose levels and for helping prevent hypoglycemic events.

Computer system/server 112 may also communicate with one or more external devices 114 such as a keyboard, a pointing device, a display 124, etc.; one or more devices that enable a user to interact with computer system/server 112; and/or any devices (e.g., network card, modem, etc.) that enable computer system/server 112 to communicate with one or more other computing devices. Such communication can occur via I/O interfaces 122 through wired connections or wireless connections such as Bluetooth and WiFi. Still yet, computer system/server 112 can communicate with one or more networks such as a local area network (LAN), a general wide area network (WAN), and/or a public network (e.g., the Internet) via network adapter 120. As depicted, network adapter 120 communicates with the other components of computer system/server 112 via bus 118. It should be understood that although not shown, other hardware and/or software components could be used in conjunction with computer system/server 112. Examples, include, but are not limited to: microcode, device drivers, redundant processing units, external disk drive arrays, RAID systems, tape drives, and data archival storage systems, etc.

Figure 2:
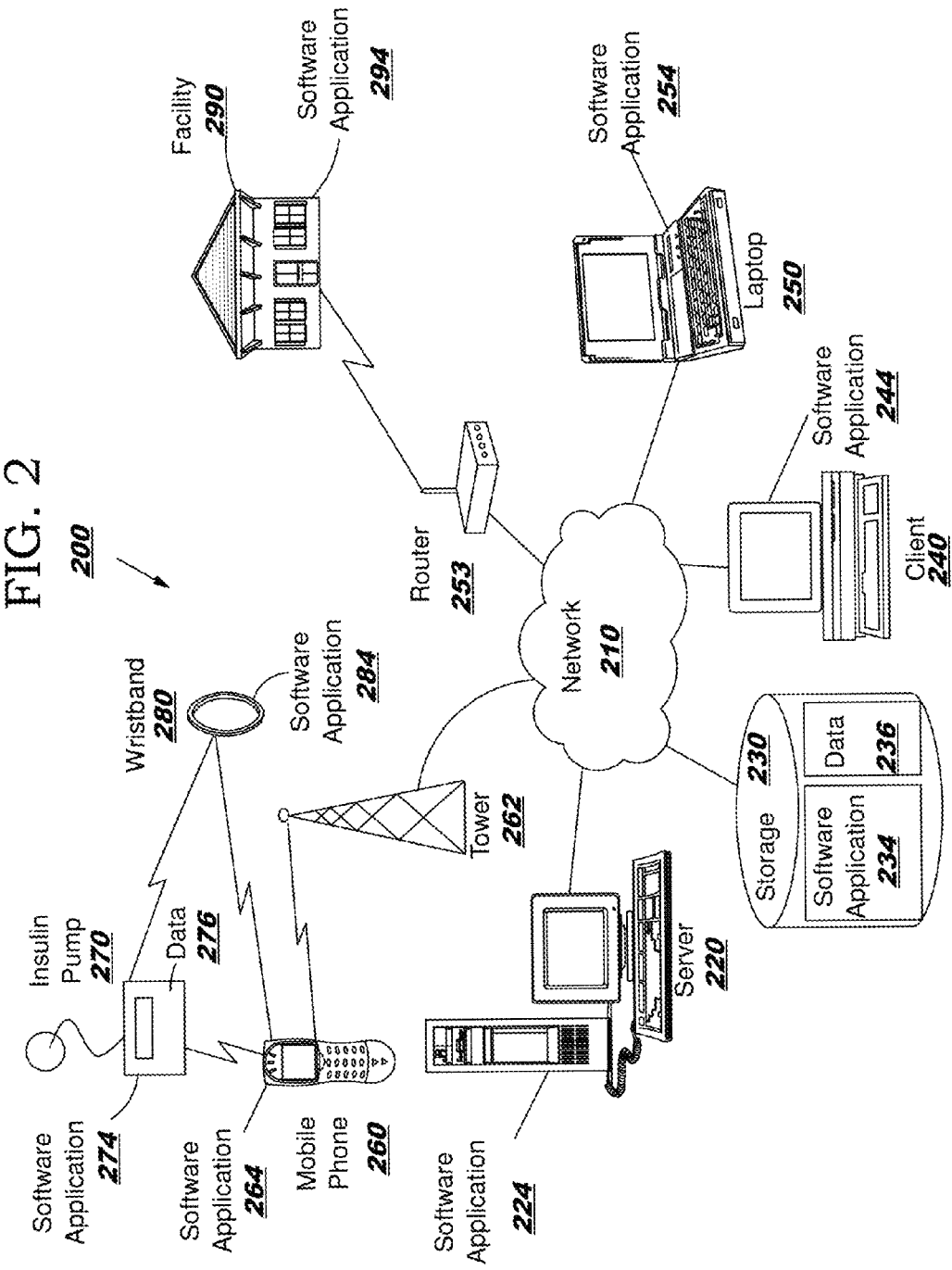
FIG. 2 is a high level block diagram of a network of data processing systems in which various embodiments may be implemented.

FIG. 2 is a high level block diagram of a network of data processing systems in which various embodiments may be implemented. Data processing environment 200 is a network of data processing systems such as described above with reference to FIG. 1. Software applications may execute on any computer or other type of data processing system in data processing environment 200. Data processing environment 200 includes network 210. Network 210 is the medium used to provide simplex, half duplex and/or full duplex communications links between various devices and computers connected together within data processing environment 200. Network 210 may include connections such as wire, wireless communication links, or fiber optic cables.

Server 220 and client 240 are coupled to network 210 along with storage unit 230. In addition, laptop 250 and facility 290 (such as a home or business) are coupled to network 210 including wirelessly such as through a network router 253. A mobile phone 260 may be coupled to network 210 through a mobile phone tower 262. An insulin pump 270 and wristband 280 may communicate with a mobile phone and with each other with a local wireless connection such as Bluetooth (a trademark of Bluetooth SIG). Data processing systems, such as server 220, client 240, laptop 250, mobile phone 260, insulin pump 270, wristband 280 and facility 290 contain data and have software applications including software tools executing thereon. Other types of data processing systems such as personal digital assistants (PDAs), smartphones, tablets and netbooks may be coupled to network 210.

Server 220 may include software application 224 such as for remotely storing and analyzing historical blood glucose levels or other software applications in accordance with embodiments described herein. Storage 230 may contain software application 234 and a content source such as data 236 for storing historical blood glucose and hypoglycemic event data. Insulin pump 270 may contain software application 274 and content source such as data 276 for storing, accessing, managing and utilizing a history of blood glucose levels. Other software and content may be stored on storage 230 or other devices for sharing among various computer or other data processing devices. Client 240 may include software application 244. Laptop 250, mobile phone 260 and wristband 280 may also include software applications 254, 264 and 284 for assisting in managing a diabetic's blood glucose levels. Facility 290 may include software applications 294. Other types of data processing systems coupled to network 210 may also include software applications. Software applications could include a web browser, email, or other software application that can manage and communicate health information such as historical data.

Server 220, storage unit 230, client 240, laptop 250, mobile phone 260, insulin pump 270, wristband 280 and facility 290 and other data processing devices may couple to network 210 using wired connections, wireless communication protocols, or other suitable data connectivity. Client 240 may be, for example, a personal computer or a network computer.

In the depicted example, server 220 may provide data, such as boot files, operating system images, and applications to client 240 and laptop 250. Client 240 and laptop 250 may be clients to server 220 in this example. Client 240, laptop 250, mobile phone 260, insulin pump 270, wristband 280 and facility 290 or some combination thereof, may include their own data, boot files, operating system images, and applications. Data processing environment 200 may include additional servers, clients, and other devices that are not shown.

In the depicted example, data processing environment 200 may be part of the Internet. Network 210 may represent a collection of networks and gateways that use the Transmission Control Protocol/Internet Protocol (TCP/IP) and other protocols to communicate with one another. At the heart of the Internet is a backbone of data communication links between major nodes or host computers, including thousands of commercial, governmental, educational, and other computer systems that route data and messages. Of course, data processing environment 100 also may be implemented as a number of different types of networks, such as for example, an intranet, a local area network (LAN), or a wide area network (WAN). FIG. 2 is intended as an example, and not as an architectural limitation for the different illustrative embodiments.

Among other uses, data processing environment 200 may be used for implementing a client server environment in which the embodiments may be implemented. A client server environment enables software applications and data to be distributed across a network such that an application functions by using the interactivity between a client data processing system and a server data processing system. Data processing environment 100 may also employ a service oriented architecture where interoperable software components distributed across a network may be packaged together as coherent business applications.

Figure 3:
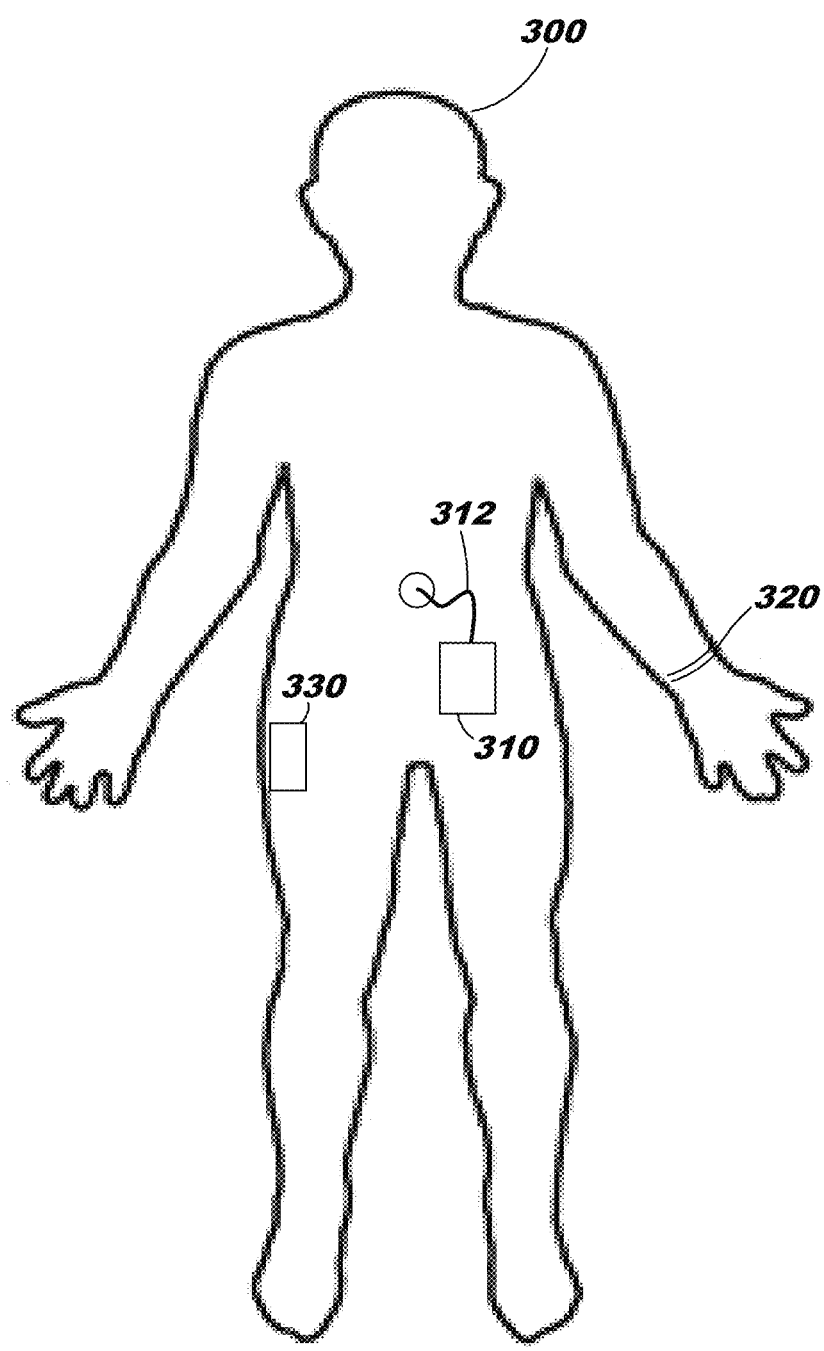
FIG. 3 is a pictorial diagram illustrating a person wearing various electronic devices in which various embodiments may be implemented.

FIG. 3 is a pictorial diagram illustrating a person wearing electronic devices in which various embodiments may be implemented. A person 300 is wearing an insulin pump 310, a wristband 320 and optionally a mobile phone 330. Other types of devices may be utilized in alternative embodiments. These devices may be in communication with each other wirelessly such as by Bluetooth. Insulin pump 310 may be worn on a belt, similar to a pager. The insulin pump includes a patient-replaceable infusion set 312 for delivering insulin from the insulin pump to a catheter inserted just under the person's skin. Wristband 320 may be worn on the person's wrist, although alternative devices may be worn as an anklet, headband, or in a pocket. Mobile phone 330 may be worn in a pocket or elsewhere on the person including on the belt or held in a person's hand.

Figure 4:
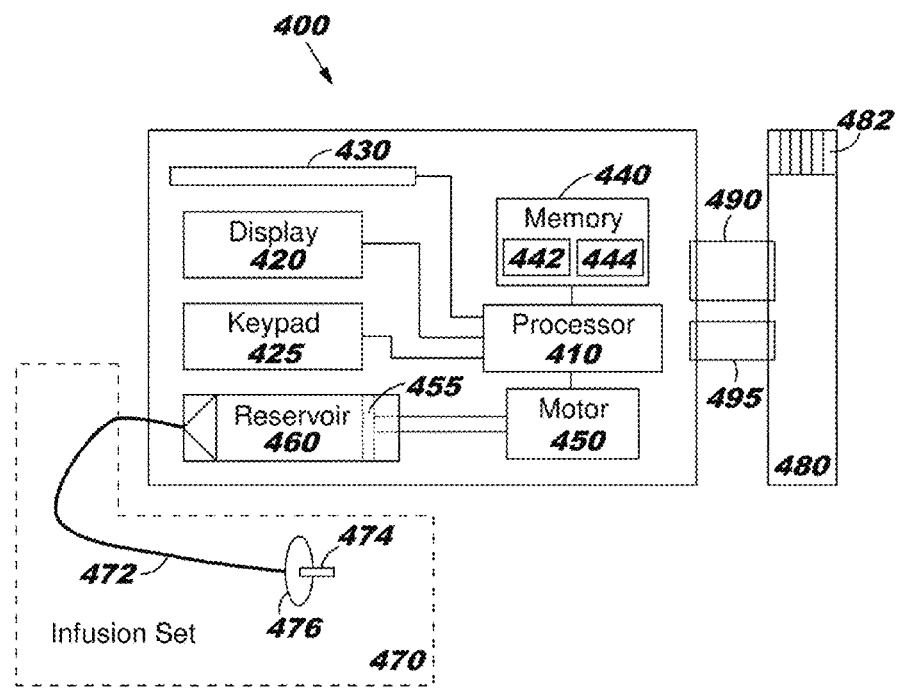
FIG. 4 is a block diagram of an insulin pump in which various embodiments may be implemented.

FIG. 4 is a diagram of an insulin pump in which various embodiments may be implemented. Insulin pump 400 is shown with a processor 410 that communicates with a user through display 420 and keypad 425. Display 420 may be an LCD display for displaying information to the wearer of the device, to a health care professional such as a physician or nurse practitioner or to a programmer or other technician. The same person may enter commands or configuration data or respond to displayed queries through keypad 425. Processor 410 may also communicate with other devices utilizing antenna 430, thereby sending or receiving data for use and/or storage in memory 440. As a result, certain processes may be performed and data may be stored by a mobile phone or other computer system in communication with the insulin pump, such as by a mobile phone application.

Processor 410 utilizes memory 440 for storing or retrieving data 442 or for utilizing programs 444 stored in memory. Processor 410 monitors a variety of factors by measuring or receiving measurements such as blood glucose measurements through a user interface or by receiving a signal from a sensor measuring heart rate. Data 442 includes historical information as well as statistical and preset parameters utilized during the operation of the insulin pump. Historical information can include information regarding the operation of the insulin pump, information regarding various environmental factors which could affect the blood glucose levels of the user, and a comprehensive history of the recent blood glucose readings that may be wirelessly transmitted from the glucometer to the insulin pump. The combination of insulin infusion amounts and blood glucose readings are collectively referred to herein as treatment factors as they are used to directly measure and adjust blood glucose amounts. Recent infusion amounts and blood glucose measurements are collectively referred to herein as recent treatment factors. Recent treatment factors include those amounts and measurements that may more directly affect predictions of current blood glucose levels such as in the past 24 hours. Older treatment factors are collectively referred to herein as historical treatment factors. Based on user-programmed instructions and data, processor 410 may signal motor 450 to push plunger 455 into insulin reservoir 460, thereby pumping insulin from the reservoir into disposable infusion set 470. The infusion set includes a tube 472, a cannula tube 474 and an adhesive patch 476. Tube 474 carries pumped insulin from reservoir 460 to cannula tube 474 for injection under the skin of the user. Adhesive patch 476 holds the cannula tube in place under the user's skin.

Every few days the user will replace the infusion set and insert the cannula tube in a different location, typically in the stomach or waist area of the user. The insulin reservoir may also be refilled at a frequency based on the size of the reservoir and the amount of insulin that is injected into the user. These two events typically coincide.

Processor 410 precisely controls motor 450 to manage the amount of insulin injected into the user. There may be a steady state amount of insulin pumped by the insulin pump during the day and night (the basal rate) as well as larger amount pumped before, during and after meals based on estimated caloric intake that is entered by the user through keypad 425 (the bolus).

Insulin pump 400 may also include a carbohydrate container 480 with a cap 482. The carbohydrate container may be strongly held to the insulin pump by connector 490 to prevent accidental removal. However, connector 490 may be weaker than the forces needed to break container 480 so that the container breaks away from the insulin pump before being broken. Connector 490 may be mechanical, magnetic, or other type of mechanism to hold container in place. In the case of predicted hypoglycemia, connector 490 may be signaled by processor 410 to allow the container to be removed easily by the user such as by reducing the strength of the magnet or by mechanically releasing a latch. As a result, carbohydrates are supplied to the person for possible consumption. In an alternative embodiment, container 480 may be in a case attached to a belt for easy access. The case may have magnetic latches that can release upon receiving signals such as when a hypoglycemic event is predicted, thereby supplying carbohydrates to the person.

The person wearing the insulin pump will also be signaled that hypoglycemia is predicted as occurring or about to occur. The user may then remove the container for consumption if the user agrees with the predicted hypoglycemia. If removed, a sensor 495 may detect that container 480 has been removed and notify processor 410. If the user has not already done so, processor 410 may then suspend the insulin pump from pumping any more insulin until the system is reset by the user. Once removed, the user may open the container by removing cap 482 and drinking the carbohydrate contents of the container. The carbohydrate contents may be a dextrose water solution or other similar high carbohydrate food that may be absorbed quickly to increase the blood glucose level of the person consuming the solution. Honey may be used due to its antibacterial properties which allow for long term storage. In particular, certain types of honey such as white tupelo honey or acacia honey may be used because they are very slow to crystallize or granulate over time compared to other honeys. White tupelo honey and acacia honey are high fructose monofloral honeys derived by bees from the tupelo tree flower or the acacia tree flower.

Figure 5:
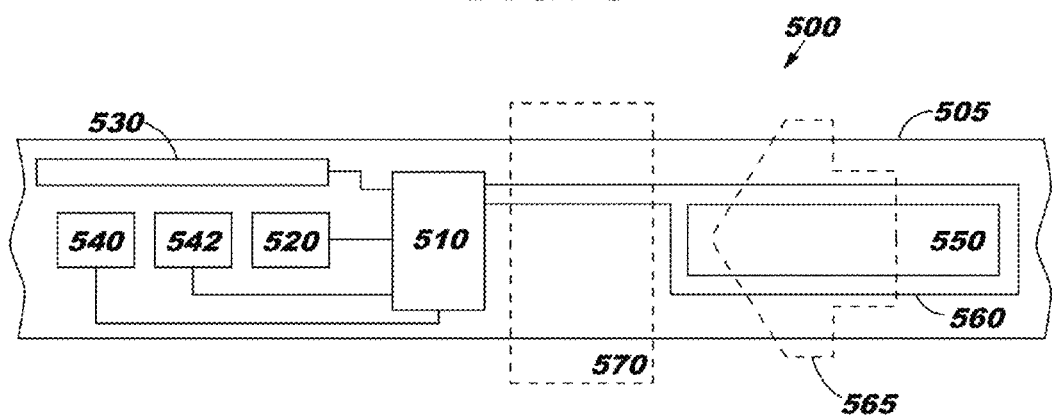
FIG. 5 is a block diagram of a wristband in which various embodiments may be implemented.

FIG. 5 is a block diagram of a wristband in which various embodiments may be implemented. For ease of display, wristband 500 is shown cut and laid flat. Wristband 500 may be constructed from a material 505 such as elastic, rubber or plastic or the material may be leather or other materials similar to watches. Wristband 500 includes a processor 510 utilizing a memory 520 to store data and programs. Processor 510 may communicate with other devices wirelessly with antenna 530. Sensors 540 and 542 may be used by processor 510 to monitor a variety of internal environmental factors that relate to the internal condition of the person (not including treatment factors) such as heart rate, body temperature, skin electrical conductivity, etc. The sensors may also be used to monitor external environmental factors that relate to the external conditions surrounding the person (not including treatment factors) such as ambient temperature and humidity, rate of motion, etc. Recent internal and external environmental factors include those amounts and measurements that may more directly affect predictions of current blood glucose levels such as in the past 24 hours. Older environmental factors are collectively referred to herein as historical environmental factors.

A container or capsule 550 may store a supply of carbohydrates (sugar or other simple carbohydrate rich substance) such as dextrose or honey. The capsule may be easily broken by the user by twisting or folding the wristband, thereby releasing or otherwise supplying carbohydrates for consumption by the user. The capsule and wristband may be constructed of plastic to be easily broken, yet not create shards unlike many glass substances. Processor 510 may use a sensor 560 to detect when the capsule has been broken. In this example, a wire 560 may encircle the capsule and would be broken if the capsule was broken, thereby signaling that event to the processor. If the wristband is constructed of an elastic material, wire 560 may also be used by processor 510 to weaken that material using heat. That is, wire 560 may be constructed with a resistive wire material which heats up when electricity is run through it, thereby weakening the elastic material making it easier for the person to break capsule 550. An optional clasp 565 may also be included for the person to use to break capsule 550 by pulling the clasp similar to a pull-tab on a soda can or by snapping or twisting the wristband apart to release the supplied carbohydrates and initiate the wireless signals.

A body 570 similar to a watch body may be attached to the wristband. Various parts described above such as processor 510 and memory 520 may be stored in the watch body for better protection from the elements. The watch body may also contain an LCD display for displaying information such as heart rate. The watch body may also include various buttons or other means for a person to enter data or respond to displayed queries. Furthermore, the watch body may contain and display additional information such as the time or GPS location of the patient.

The insulin pump and wristband may communicate wirelessly with each other or with other devices such as a mobile phone. Various sensors in or various capabilities of mobile phone or other computer system in communication with the wristband may be useful in the below processes. For example, a GPS unit or accelerometer in the mobile phone may be used to identify the location or movement by the person. In addition, memory and processing power of the mobile phone or other computer system may be used for storing or analyzing data such as for predicting a hypoglycemic event. An application in the mobile phone may be useful to assist or manage these processes. As will be described below, these devices may use these wireless capabilities to better communicate with the user, with family, medical or emergency personnel, or with programs and date stored remotely.

Figure 6A:
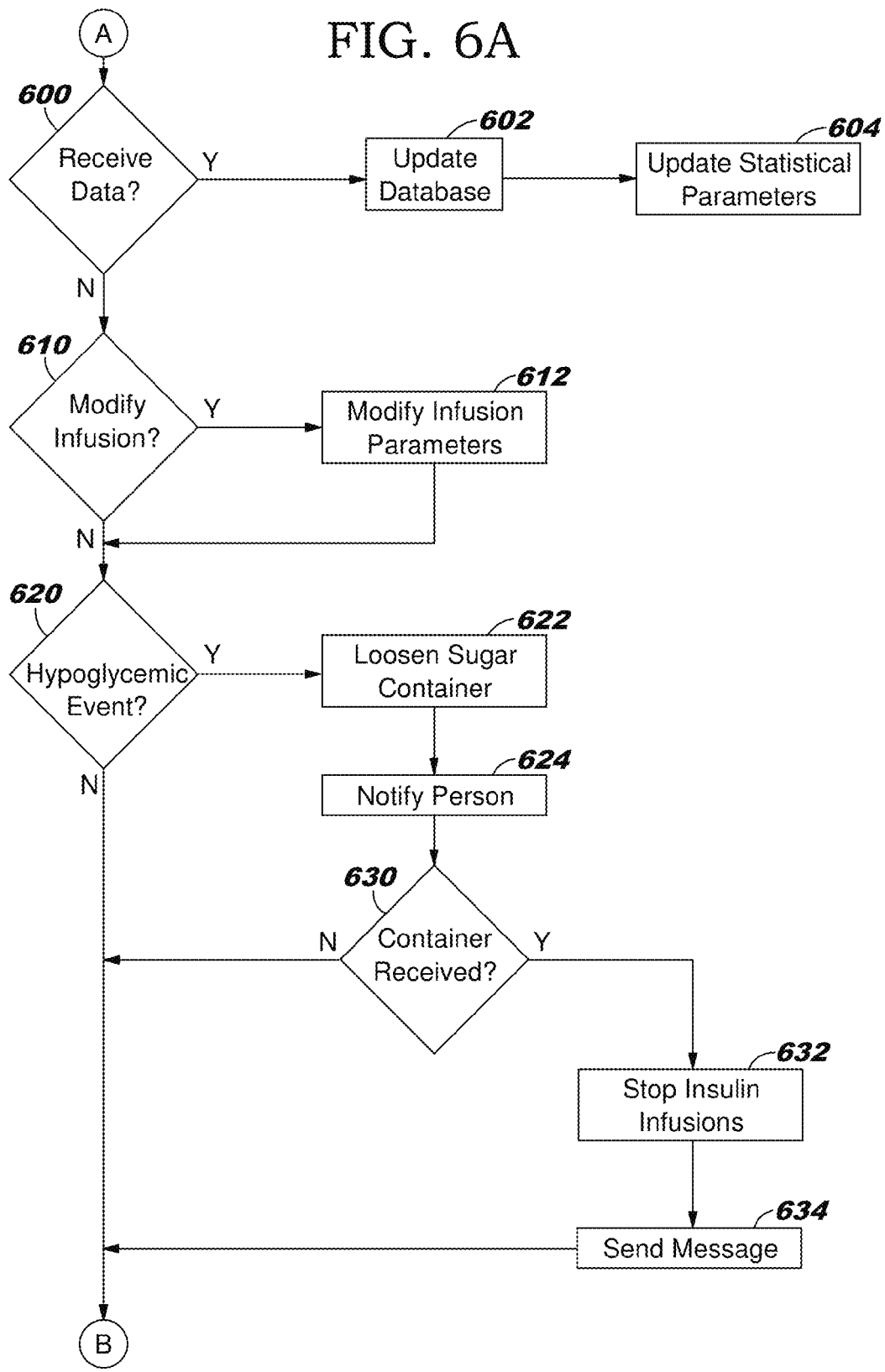
FIGS. 6A and 6B illustrate a flow diagram of the operation of the insulin pump in which various embodiments may be implemented.
Figure 6B:
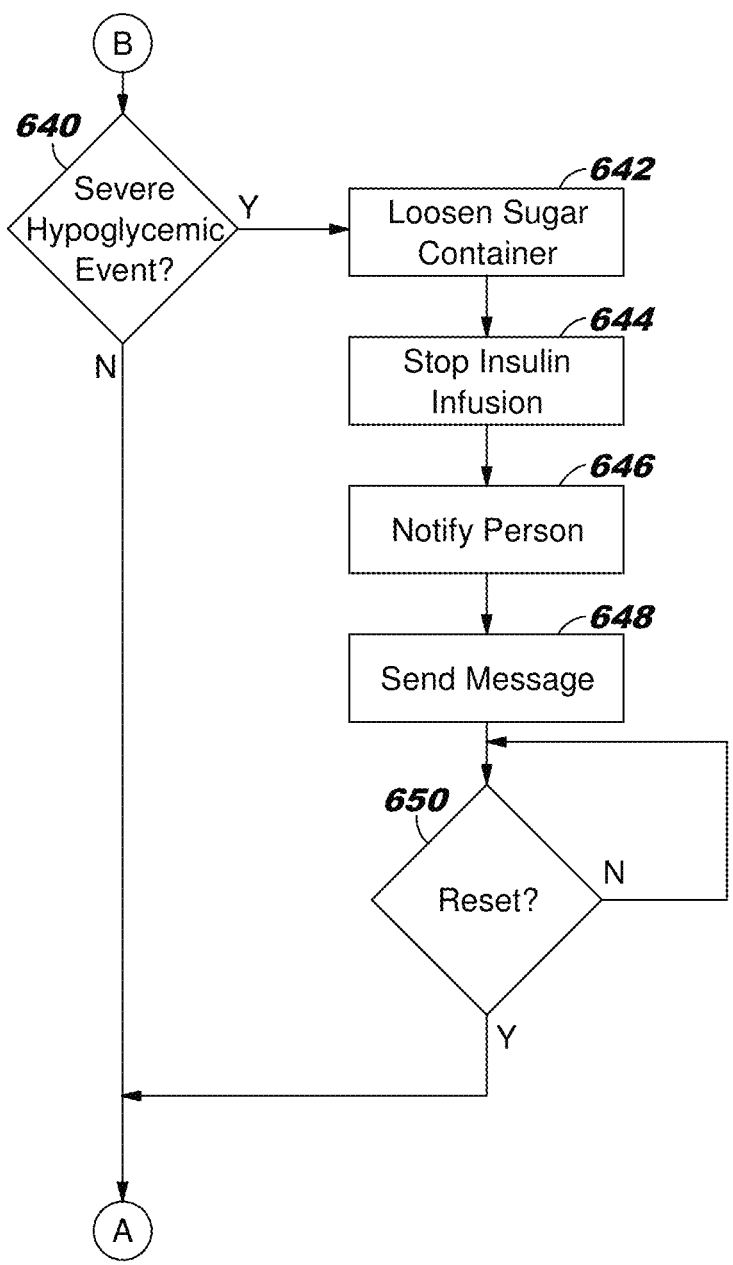

FIGS. 6A and 6B illustrate a flow diagram of the operation of the insulin pump in which various embodiments may be implemented. This flow diagram describes the operation of a program 444 stored in memory 440 of insulin pump 400. Alternatively, this program or portions thereof may be an application stored and processed by a mobile phone or other computer system in communication with the insulin pump. This program is used to manage the operation of the insulin pump including handling input data and predicting hypoglycemic events.

In a first step 600, the insulin pump processor 410 monitors various factors of a person and determines whether any data is being received. The data may be received from a person entering information through keypad 425, from a wireless connection with wristband 500, mobile phone 330 (such as rate of motion information derived from GPS data), or from other sources such as a blood glucose meter (glucometer) or sensors on the wristband. This data may be insulin infusion amounts, blood glucose measurements, and recent environmental factors including internal environmental factors such as heart rate information, body temperature, sweating, skin electrical conductivity, etc. and external environmental factors such as ambient temperature and humidity, rate of motion, etc. If no data is received, then processing continues to step 610. If such data is received, then in step 602 a database of historical information is updated in memory 442. In addition, in step 604 certain historical and statistical parameters are updated based on the data being input. For example, certain blood glucose running averages may be modified based on blood glucose data being input. Processing then continues to step 610.

In step 610, it is determined whether the infused amount of insulin should be modified. This modification may be time based. That is, given the amount of time since the last meal, the infusion amount may be reduced to a basal rate. Also, recently input data such as calories consumed in a meal may be used to increase the infusion amount of insulin. In general, based on time, input data, historical information stored in memory, and recent modifications to statistical parameters based on environmental factors, the infusion amount may be modified in step 612. Regardless whether the infusion amount is changed or not, processing then proceeds to step 620.

In step 620, it is determined whether a hypoglycemic event is anticipated or being experienced (i.e. predicted). This determination is made based on recently input data, historical data, statistical parameters, treatment factors, environmental factors, etc. Data can include time since the last meal, amount of insulin infused, recent blood glucose measurements, etc. Environmental factors can include internal environmental factors such as heart rate, body temperature, perspiration, skin electrical conductivity, etc. and external environmental factors including ambient temperature and humidity, rate of motion, etc. If not, then processing proceeds to step 640. If a hypoglycemic event is predicted, then in step 622 the container containing carbohydrates is loosened for ease of access by the person thereby supplying carbohydrates to the person. That is, the container of carbohydrates is supplied (e.g. made available) to the person for possible consumption. The person is notified in step 624 of the anticipated hypoglycemic event. This notification can be by a message on the insulin pump display, by an audio alarm, by vibration, etc. The message can also be sent to the person through the person's mobile phone, thereby taking advantage of the many features of the mobile phone such as audio and vibrating capabilities.

Once notified, the person has several options. The person may access and consume the carbohydrates supplied in the container. The person may alternatively or additionally consume some carbohydrates such as a snack bar, a soda, or other similar material. If consumed, the person should enter an estimate of the carbohydrates consumed into the insulin pump in step 600 above. The person may also take a simple blood test using a glucometer and enter that information into the insulin pump in step 600 above. That would allow the person to confirm or not whether the estimated potential hypoglycemic event is occurring. The person may also cease exercising, seek assistance, or do other steps to reduce the possibility of a hypoglycemic event.

Once the person has been notified, it is determined in step 630 whether the person has accessed container 480 or 550 for consumption of the supplied carbohydrates. This can be detected by sensors 495 or 560. If not, then processing continues to step 640. If the container is accessed, that indicates that the person agrees with the predicted hypoglycemic event and needed to consume the carbohydrates in the container. It also indicates that the person does not have other alternatives readily available and may need assistance. In the case that the container is accessed, the insulin infusions are stopped in step 632 and a message may be sent to a third party through the mobile phone in step 634. That message may be a text message to a family member or a health care individual sent by the mobile phone as instructed wirelessly by the insulin pump. Processing then proceeds to step 640.

In step 640 the insulin pump determines whether the person may be experiencing a severe hypoglycemic event and may be unresponsive as a result. Factors can include whether the user has responded to the notification in step 624 above, whether the expected current blood glucose level is below an acceptable minimum, etc. If not, then processing can return to step 600 above. If a sever hypoglycemic event is predicted, then in step 642 the container is loosened thereby supplying carbohydrates to the person, all insulin infusions are ceased, the person is notified of the predicted condition in step 646 and a message is sent to family and/or health care professionals in step 648. The message may include location information, particularly if the message is sent through the mobile phone with GPS capabilities.

The insulin pump then enters a suspended or standby state in step 650 where it does not perform any more actions, including not delivering the basal rate of insulin because the user may be confused and forget to suspend the pump, until it is reset by the user such as by pressing a reset button or keying a password into the insulin pump keypad. During this standby state, the insulin pump may be emitting loud high pitched tones to alert anyone nearby, may play a repeating message such as "I am a diabetic person in distress. Please either seek emergency help of help me ingest a sugary substance to reverse my condition", and may be sending additional messages with location information through the mobile phone. The insulin pump may also be displaying helpful information on the insulin pump display that is easily visible in case any passerby comes to the aid of the user.

Figure 7:
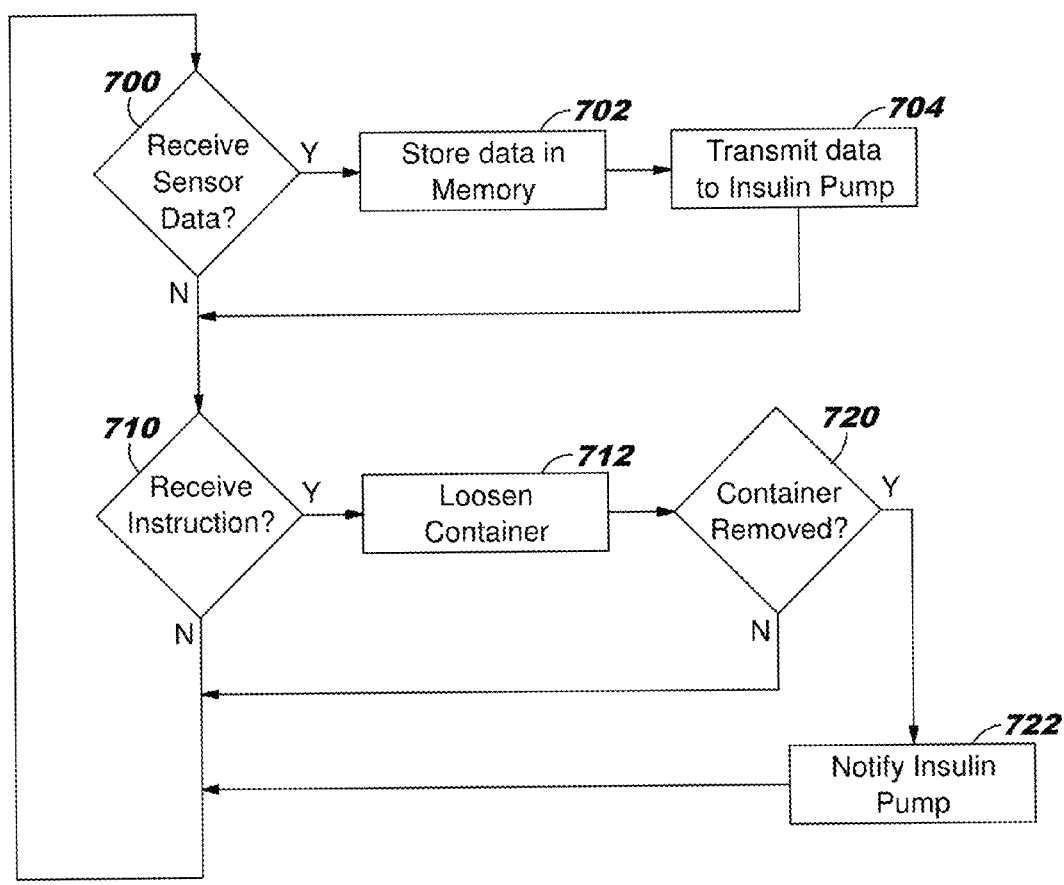
FIG. 7 is a flow diagram of the operation of the wristband in which various embodiments may be implemented.

FIG. 7 is a flow diagram of the operation of the wristband in which various embodiments may be implemented. This flow diagram describes the operation of a program 444 stored in memory 440 of wristband 500. Alternatively, this program or portions thereof may be an application stored and processed by a mobile phone or other computer system in communication with the wristband and/or the insulin pump. This program is used to manage the operation of the wristband including providing sensor data to the insulin pump and responding to instructions from the insulin pump. The wristband may be utilized by the diabetic in lieu of container 480.

In a first step 700, wristband processor 510 monitors various factors of a person and determines whether it has received any sensor data such as heart rate information or other environmental factors from sensors 540 and 542. If not, then processing continues to step 710. If yes, then in step 702 that information is stored in memory 520. That information may be accumulated with prior stored information to provide running averages or the like. If the wristband has a body with a display, that information may be displayed for the user to read. Subsequently, in step 704 that information may be transmitted to the insulin pump wirelessly. Processing then continues to step 710.

In step 710, wristband processor 510 determines whether it has received an instruction wirelessly on antenna 530 from the insulin pump. If not, then processing returns to step 700. If yes, then in step 712 the processor may loosen container 550 thereby supplying carbohydrates to the person such as by heating sensor wire 560. That is, the container of carbohydrates is supplied (e.g. made available) to the person for possible consumption. Subsequently in step 720 processor 510 then determines through sensor 560 whether container 550 has been accessed by the user for consumption. If the container is removed, that indicates that the person agrees with the predicted hypoglycemic event and needed to consume the carbohydrates in the container. It also indicates that the person does not have other alternatives readily available and may need assistance. If the container is not accessed, then processing returns to step 700. If the container is accessed, then in step 722 the insulin pump is notified wirelessly through antenna 530 that container 550 has been removed by the user. Processing then returns to step 700.

Figure 8:
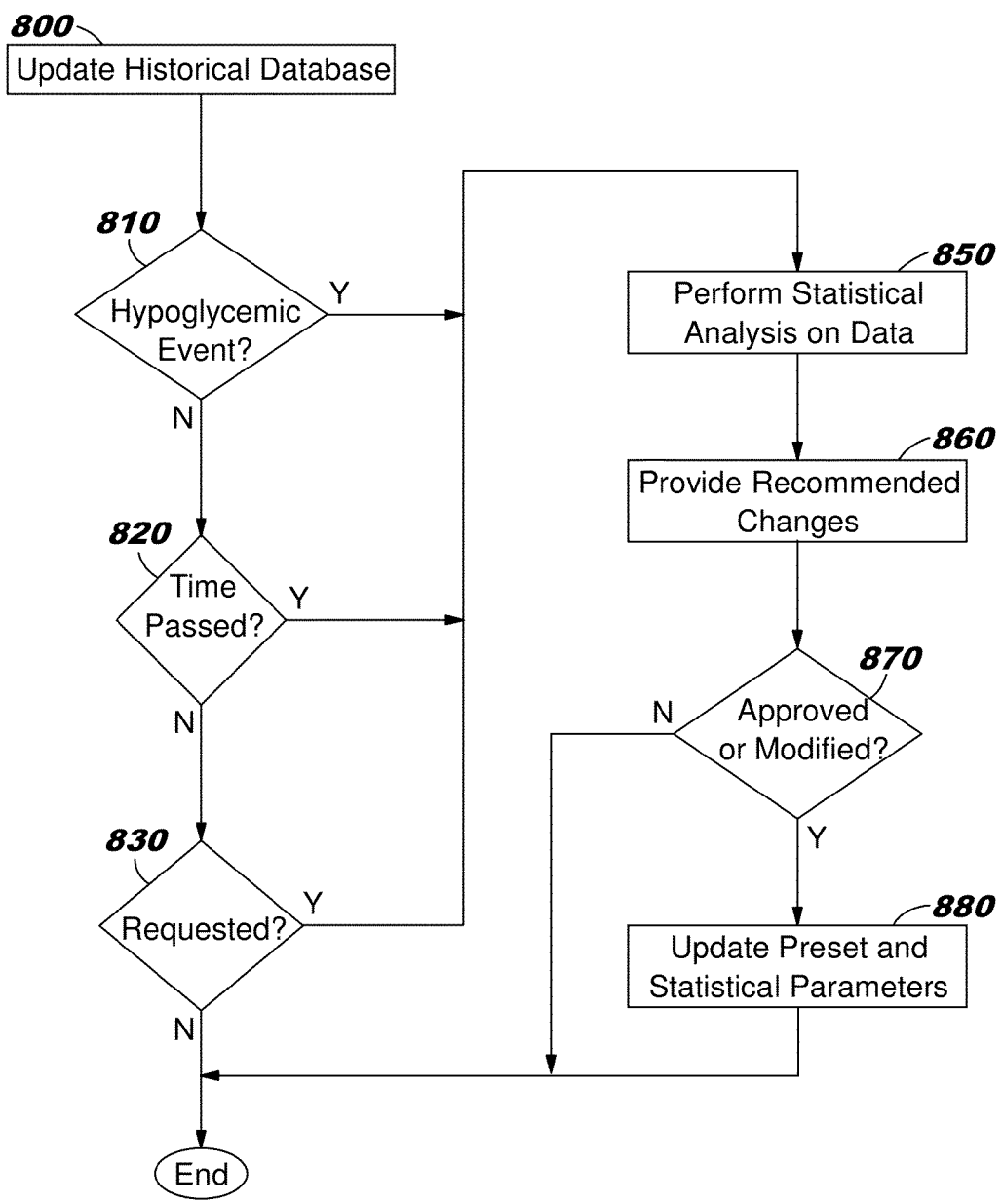
FIG. 8 illustrates a flow diagram of the management of a historical database in which various embodiments may be implemented.

FIG. 8 illustrates a flow diagram of the management of a historical database in which various embodiments may be implemented. The historical database may be contained within the insulin pump, on a mobile phone, or it may be stored remotely such as on a server. In a first step 800, the database is updated with any new data such as insulin infusion amounts, glucometer test results, carbohydrate consumption as entered by the user, hypoglycemic events, and other environmental factors. If the database is stored remotely such as on a server, the data may be uploaded periodically by the user across the internet or certain events may be uploaded through messages such as when a hypoglycemic event occurs.

Subsequently it is determined in step 810 whether a hypoglycemic event has recently occurred. If yes, then processing continues to step 850 for performing certain analytics, otherwise processing continues to step 820. In step 820 it is determined whether sufficient time has passed that certain analytics need to be performed. If yes, then processing continues to step 850, otherwise processing continues to step 830. In step 830 it is determined whether a health care professional has requested that certain analytics be performed. If yes, then processing to step 850, otherwise processing ceases.

In step 850, certain statistical analysis is performed to generate statistical parameters based on treatment factors and environmental factors. This analysis can include determining how much insulin is needed for the person at rest, finding the correlation between certain activities and actions by the user and the amount of blood glucose used by those activities and actions, etc. For example, the amount of blood glucose utilized by the person at a given heart rate may be statistically determined for predictive purposes. If a server historical database is utilized which contains data from multiple individuals, this statistical analysis may utilize that additional information for potentially better results.

Subsequently in step 860 the results of this statistical analysis is used to generate recommended changes to certain preset parameters. For example, the basal rate of insulin infused may need to be modified. In addition, certain correlations may be better estimated such as the amount of blood glucose used when the diabetic's heart rate is elevated such as from exercise. Processing then continues to step 870 where it is determined whether a health care professional approved the recommended changes or modifications thereto. The healthcare professional may be contacted through the internet, by phone or in person depending on circumstances. If not, then processing ceases. Alternative embodiments may allow certain limited changes to statistical and preset parameters without approval of a health care professional. Otherwise the approved statistical parameters are updated in step 880. If the historical database is remotely stored from the insulin pump, then this would include downloading the statistical parameters to the insulin pump across the internet without necessitating a visit from the person to the health care professional, thereby reducing health care costs. Subsequently processing would cease until the next update to the historical database.

Figure 9:
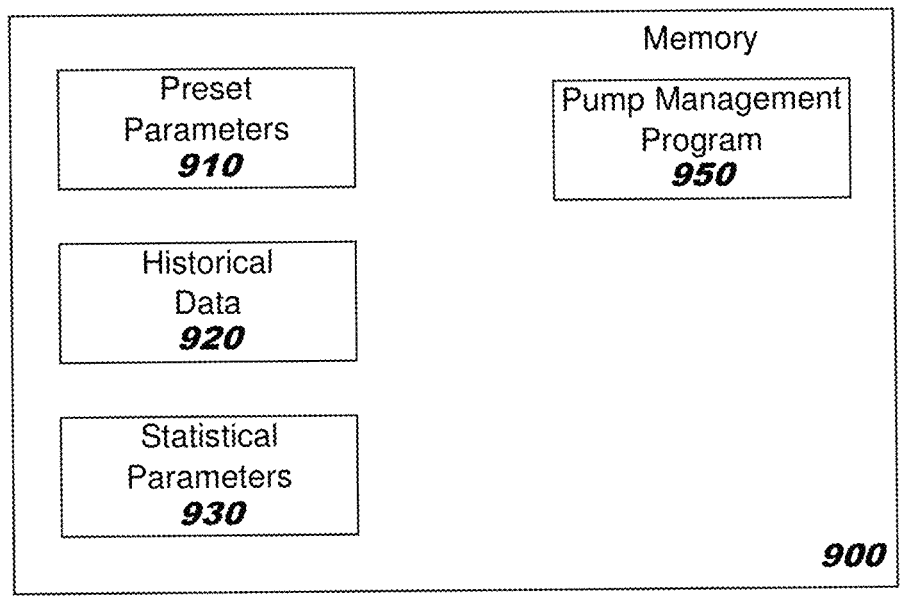
FIG. 9 is a block diagram of a various data which may be stored in insulin pump memory in which various embodiments may be implemented.

FIG. 9 is a block diagram of a various types of data which may be stored in insulin pump memory (or alternatively mobile phone memory, wristband memory, or other remote memory) in which various embodiments may be implemented. This memory 900 can correspond with memory 440 described with reference to FIG. 4 above or it can be stored remotely on a mobile phone or a server database such as data 236 of FIG. 2 above. This memory is utilized by the memory pump processor to store data and programs that control the operation of the insulin pump. This data may be backed up or supplemented remotely such as by server storage 230 described above with reference to FIG. 2.

Memory 900 includes a variety of data types based on treatment factors and environmental factors including but not limited to preset parameters 910, historical data 920 and statistical parameters 930. Other types of data may be stored in memory and utilized by the insulin pump.

Present parameters 910 may include a basal rate of insulin infusion, an amount and rate of insulin infusion for a given predicted caloric intake by the user, a minimum blood glucose level before invoking a predicted hypoglycemia condition or a predicted severe hypoglycemic condition, or many other useful parameters for managing the operation of the insulin pump. Some of these parameters may be preset at the factory, set by a health care professional and not modifiable by a user, or modifiable by a user.

Historical data 920 may include data related to prior hypoglycemic events, sensor data received from a wrist band such as heart rate, the amount of insulin infused since the last refill of the insulin reservoir, etc. Historical data may also include certain accumulations and running averages on sensor and other data on environmental factors including internal environmental factors such as heart rate, body temperature, perspiration, skin electrical conductivity, and external environmental factors such as ambient temperature and humidity, rate of motion, etc.

Statistical parameters 930 may include correlations and other statistically analyzed data derived from historical data. These statistical parameters may be useful in predicting current and future blood glucose levels as well as for adjusting the preset parameters. For example, an increased heart rate will indicate that the person is using more calories than a basal rate. As a result, blood glucose levels could drop. In addition, the correlation between heart rate and caloric output and drop in blood glucose levels may not be linear. That is, a heart rate increase of 10% above a basal heart rate may result in blood glucose levels dropping 1 mg/dl per hour, but a heart rate increase of 30% may result in blood glucose levels dropping 10 mg/dl per hour for this person. To utilize this information, a formula or a table may be statistically generated from historical data. This formula or table may then be utilized for predicting current and future blood glucose levels. This same analysis may be performed on other types of data such as ambient temperature and humidity, body temperature, rate of motion, perspiration, skin electrical conductivity, etc.

The above described data may be utilized by processor 610 to predict a potential hypoglycemic event and then respond accordingly. For example, if a user has not eaten for 6 hours, has experienced higher than average heart rate and body temperature (such as by exercising), then a hypoglycemic event may be predicted.

Also shown in memory 900 is pump management program 950. This software is used by the processor to manage the operation of the insulin pump and utilize the data stored in memory.

The invention can take the form of an entirely software embodiment, or an embodiment containing both hardware and software elements. In a preferred embodiment, the invention is implemented in software or program code, which includes but is not limited to firmware, resident software, and microcode.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, microcode, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM), or Flash memory, an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing. Further, a computer storage medium may contain or store a computer-readable program code such that when the computer-readable program code is executed on a computer, the execution of this computer-readable program code causes the computer to transmit another computer-readable program code over a communications link. This communications link may use a medium that is, for example without limitation, physical or wireless.

A data processing system suitable for storing and/or executing program code will include at least one processor coupled directly or indirectly to memory elements through a system bus. The memory elements can include local memory employed during actual execution of the program code, bulk storage media, and cache memories, which provide temporary storage of at least some program code in order to reduce the number of times code must be retrieved from bulk storage media during execution.

A data processing system may act as a server data processing system or a client data processing system. Server and client data processing systems may include data storage media that are computer usable, such as being computer readable. A data storage medium associated with a server data processing system may contain computer usable code such as for managing blood glucose and for predicting and managing hypoglycemic events. A client data processing system may download that computer usable code, such as for storing on a data storage medium associated with the client data processing system, or for using in the client data processing system. The server data processing system may similarly upload computer usable code from the client data processing system such as a content source. The computer usable code resulting from a computer usable program product embodiment of the illustrative embodiments may be uploaded or downloaded using server and client data processing systems in this manner.

Input/output or I/O devices (including but not limited to keyboards, displays, pointing devices, etc.) can be coupled to the system either directly or through intervening I/O controllers.

Network adapters may also be coupled to any of the data processing systems described herein to enable those data processing systems to become coupled to other data processing systems or remote printers or storage devices through intervening private or public networks. Modems, cable modem and Ethernet cards are just a few of the currently available types of network adapters.

The description of the present invention has been presented for purposes of illustration and description, and is not intended to be exhaustive or limited to the invention in the form disclosed. Many modifications and variations will be apparent to those of ordinary skill in the art. The embodiment was chosen and described in order to explain the principles of the invention, the practical application, and to enable others of ordinary skill in the art to understand the invention for various embodiments with various modifications as are suited to the particular use contemplated.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A method of managing a blood glucose level of a person comprising:
   providing a device worn exterior to the person for monitoring a set of treatment factors, a set of internal environmental factors that relate to the internal condition of the person, and a set of external environmental factors that relate to the external conditions surrounding the person and which affects a blood glucose level for the person, the device including an insulin reservoir and a carbohydrate container;
   capturing and storing a history of the set of treatment factors and the sets of internal and external environmental factors;
   performing statistical analysis on the stored history of the set of treatment factors and the sets of internal and external environmental factors;
   updating preset statistical parameters including insulin infusion amounts based on the statistical analysis on the stored history;
   predicting changes in the current blood glucose level for the person since a last blood glucose measurement based on the statistical analysis on the stored history of the set of treatment factors and the sets of internal and external environmental factors and treatment factors, and on treatment factors, internal and external environmental factors monitored since the last blood glucose measurement;
   based on the predicted current blood glucose level, providing a first signal to the device to deliver a determined amount of insulin, based on the updated preset statistical parameters of insulin infusion amounts, from the insulin reservoir to the person; and
   responsive to predicting the current blood glucose level for the person dropping lower than a predetermined minimum value, providing a second signal to a material holding the carbohydrate container to release the carbohydrate container, thereby supplying carbohydrates to the person.

2. The method of claim 1 wherein the stored history of set of treatment factors and the sets of internal and external environmental factors includes data from multiple individuals for use in performing statistical analysis and updating preset statistical parameters including insulin infusion amounts.

3. The method of claim 1 wherein the container is contained within a bracelet which may be easily opened to access the container and which may be worn by the person; and wherein the second signal is provided wirelessly to the bracelet to weaken an element holding the carbohydrate container to release the carbohydrate container, thereby supplying carbohydrates to the person.

4. The method of claim 1 further comprising providing a signal to the person in response to the predicted current blood glucose level dropping lower than the predetermined minimum value.

5. The method of claim 4 further comprising transmitting a message to other persons in response to the predicted current blood glucose level dropping lower than the predetermined minimum value, the message including a location of the person.

6. The method of claim 4 further comprising determining whether the person has accessed the carbohydrates, and responsive to a positive determination transmitting a message to other persons, the message including a location of the person.

7. The method of claim 4 wherein the device includes an insulin pump and wherein any infusion of insulin is suspended in response to the predicted current blood glucose level dropping lower than the predetermined minimum value.

8. The method of claim 1 further comprising generating a corresponding set of associated effects on blood glucose levels from the history of the set of treatment factors and the sets of internal and external environmental factors.

9. The method of claim 8 wherein the set of treatment factors includes one or more items selected from the group of insulin basal rate, insulin bolus amounts, and blood glucose measurements, and wherein the set of internal environmental factors includes one or more items selected from the group of heart rate, body temperature, rate of motion, perspiration, and skin electrical conductivity, and wherein the set of external environmental factors which affect and for predicting the current blood glucose level for the person includes one or more items selected from the group of ambient temperature and ambient humidity.

10. The method of claim 9 wherein the set of treatment factors and the set of environmental factors are stored remotely for access and analysis by a health care provider.

11. A computer usable program product comprising a non-transitory computer usable storage medium including computer usable code for use in managing a blood glucose level of a person, the computer usable program product comprising code for performing the steps of:
    communicating with a device worn exterior to the person for monitoring a set of treatment factors, a set of internal environmental factors that relate to the internal condition of the person, and a set of external environmental factors that relate to the external conditions surrounding the person and which affects a blood glucose level for the person, the device including an insulin reservoir and a carbohydrate container;
    capturing and storing a history of the set of treatment factors and the sets of internal and external environmental factors;
    performing statistical analysis on the stored history of the set of treatment factors and the sets of internal and external environmental factors;

updating preset statistical parameters including insulin infusion amounts based on the statistical analysis on the stored history;

predicting changes in the current blood glucose level for the person since a last blood glucose measurement based on the statistical analysis on the stored history of the set of treatment factors and the sets of internal and external environmental factors, and on treatment factors, internal and external environmental factors monitored since the last blood glucose measurement;

based on the predicted current blood glucose level, providing a first signal to the device to deliver a determined amount of insulin, based on the updated preset statistical parameters of insulin infusion amounts, from the insulin reservoir to the person; and responsive to predicting the current blood glucose level for the person dropping lower than a predetermined minimum value, providing a second signal to a material holding the carbohydrate container to release the carbohydrate container, thereby supplying carbohydrates to the person.

12. The computer usable program product of claim 11 further comprising code for providing a signal to the person in response to the predicted current blood glucose level dropping lower than the predetermined minimum value and transmitting a message to other persons in response to the predicted current blood glucose level dropping lower than the predetermined minimum value, the message including a location of the person.

13. The computer usable program product of claim 11 wherein the device includes an insulin pump and wherein any infusion of insulin is suspended in response to the predicted current blood glucose level dropping lower than the predetermined minimum value.

14. The computer usable program product of claim 11 wherein the container is contained within a bracelet which may be easily opened to access the container and which may be worn by the person; and wherein the second signal is provided wirelessly to the bracelet to weaken an element holding the carbohydrate container to release the carbohydrate container, thereby supplying carbohydrates to the person.

15. The computer usable program product of claim 11 further comprising code for generating a corresponding set of associated effects on blood glucose levels from the history of the set of treatment factors and the sets of internal and external environmental factors, wherein the set of treatment factors includes one or more items selected from the group of insulin basal rate, insulin bolus amounts, and blood glucose measurements, and wherein the set of internal environmental factors includes one or more items selected from the group of heart rate, body temperature, rate of motion, perspiration, and skin electrical conductivity, and wherein the set of external environmental factors which affect and for predicting the current blood glucose level for the person includes one or more items selected from the group of ambient temperature and ambient humidity.

16. A data processing system for managing a blood glucose level of a person, the data processing system comprising:

a processor; and a memory storing program instructions which when executed by the processor execute the steps of:

communicating with a device worn exterior to the person for monitoring a set of treatment factors, a set of internal environmental factors that relate to the internal condition of the person, and a set of external environmental factors that relate to the external conditions surrounding the person and which affects a blood glucose level for the person, the device including an insulin reservoir and a carbohydrate container;

capturing and storing a history of the set of treatment factors and the sets of internal and external environmental factors;

performing statistical analysis on the stored history of the set of treatment factors and the sets of internal and external environmental factors;

updating preset statistical parameters including insulin infusion amounts based on the statistical analysis on the stored history;

predicting changes in the current blood glucose level for the person since a last blood glucose measurement based on the statistical analysis on the stored history of the set of treatment factors and the sets of internal and external environmental factors, and on treatment factors, internal and external environmental factors monitored since the last blood glucose measurement;

based on the predicted current blood glucose level, providing a first signal to the device to deliver a determined amount of insulin, based on the updated preset statistical parameters of insulin infusion amounts, from the insulin reservoir to the person; and responsive to predicting the current blood glucose level for the person dropping lower than a predetermined minimum value, providing a second signal to a material holding the carbohydrate container to release the carbohydrate container, thereby supplying carbohydrates to the person.

17. The data processing system of claim 16 further comprising generating a corresponding set of associated effects on blood glucose levels from the history of the set of treatment factors and the sets of internal and external environmental factors, wherein the set of treatment factors includes one or more items selected from the group of insulin basal rate, insulin bolus amounts, and blood glucose measurements, and wherein the set of internal environmental factors includes one or more items selected from the group of heart rate, body temperature, rate of motion, perspiration, and skin electrical conductivity, and wherein the set of external environmental factors which affect and for predicting the current blood glucose level for the person includes one or more items selected from the group of ambient temperature and ambient humidity.

18. The data processing system of claim 16 further comprising program instructions for providing a signal to the person in response to the predicted current blood glucose level dropping lower than the predetermined minimum value and transmitting a message to other persons in response to the predicted current blood glucose level dropping lower than the predetermined minimum value, the message including a location of the person.

19. The data processing system of claim 18 wherein the device includes an insulin pump and wherein any infusion of insulin is suspended in response to the predicted current blood glucose level dropping lower than the predetermined minimum value.

20. The data processing system of claim 19 wherein the container is contained within a bracelet which may be easily opened to access the container and which may be worn by the person; and wherein the second signal is provided wirelessly to the bracelet to weaken an element holding the carbohydrate container to release the carbohydrate container, thereby supplying carbohydrates to the person.

\* \* \* \* \*